United States Patent [19]

Rademacher

[11] Patent Number: 5,016,292

[45] Date of Patent: May 21, 1991

[54] COMBINATION GAMMA, ULTRAVIOLET AND X-RADIATION GOGGLES

[76] Inventor: Mark Rademacher, 3222 Royal Dr., Cameron Park, Calif. 95682

[21] Appl. No.: 448,015

[22] Filed: Dec. 7, 1989

[51] Int. Cl.$^5$ .............................................. A61F 9/02
[52] U.S. Cl. ......................................... 2/431; 2/448; 250/516.1; 128/858
[58] Field of Search ................... 2/432, 431, 9, 2.1 A, 2/15, 426, 448, 450, 439; 250/516.1, 515.1; 128/858; 351/44; 350/1.6

[56] References Cited

U.S. PATENT DOCUMENTS

| | | | |
|---|---|---|---|
| 4,021,862 | 5/1977 | Glasser et al. ........................... | 2/431 |
| 4,024,405 | 5/1977 | Szot ....................................... | 2/15 X |
| 4,286,170 | 8/1981 | Moti ............................... | 250/516.1 X |
| 4,635,625 | 1/1987 | Teeple ................................. | 2/15 X |
| 4,640,685 | 2/1987 | Croll ............................. | 250/515.1 X |
| 4,670,915 | 6/1987 | Evans ................................. | 2/443 X |
| 4,701,129 | 11/1987 | Hazard ......................... | 250/515.1 X |
| 4,758,079 | 7/1988 | Bledsoe ................................ | 351/44 |
| 4,797,956 | 1/1989 | Boyce ................................. | 128/858 X |
| 4,938,233 | 7/1990 | Orrison, Jr. ................... | 250/516.1 X |

OTHER PUBLICATIONS

Catalog G-5 (pp. 34 and 48) from Nuclear Associates for Goggles and p. 14 (lead-vinyl).
Oral Surgery, Antoku et al., 41(2), pp. 251-260 (1976).
Rad. Physics, Littleton et al., 129, pp. 795-798 (1978).
New England J. of Med., Taylor et al., 319(22), pp. 1429-1433 (1988).
Docum. Ophthal., Zigman, 55, pp. 375-391 (1983).
Path. of the Eye, vonDomarus et al., pp. 227-234, Springer-Verlag, NY (1986).
Ophthal., Chylack, Jr., 91(6), pp. 596-601 (1984).
Clear-Pb Technical Data from Nuclear Associates.

*Primary Examiner*—Peter Nerbun
*Attorney, Agent, or Firm*—James M. Ritchey

[57] ABSTRACT

Safety goggles that effectively filter possibly dangerous levels of all types of cataractogenic radiation including near blue light, UV-A, B, and C, Gamma, and X-radiation are disclosed comprising an UV, Gamma, and X-ray radiopaque frameless leaded polymer lens formed to curve over a user's face having a radiolucent polymer nose rest and ear pieces and a radiopaque boot extending from the lens to proximate the user's face to produce a vented peripheral enclosure to cover both eyes of the user and shield the user's eyes from all angles of harmful radiation exposure, but allow unobstructed forward and peripheral vision.

13 Claims, 4 Drawing Sheets

FIG.-7
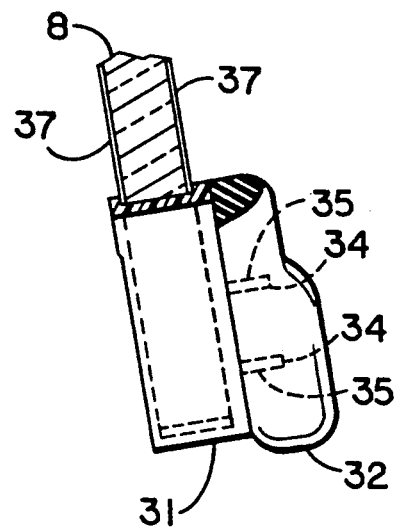
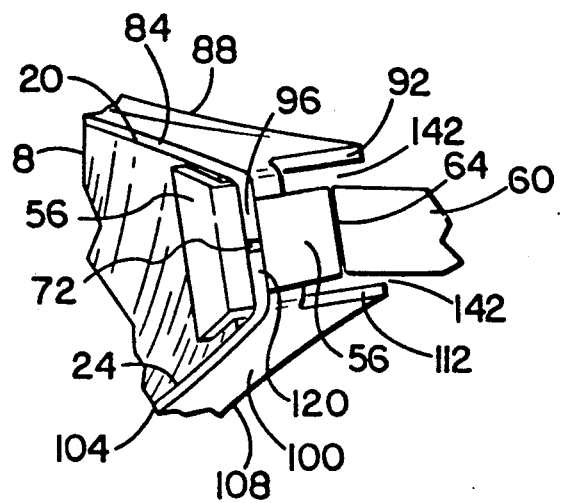
FIG.-8

COMBINATION GAMMA, ULTRAVIOLET AND X-RADIATION GOGGLES

BACKGROUND OF THE INVENTION

1. Field of the Invention

Individuals subject to cataractogenic radiation, both short and long term exposure, suffer eye damage. This damage manifests itself primarily as a tumor and a nuclear or cortical lens cataract. The lens cataractogenic dose has been recently identified as 200 REMS with Gamma or X-radiation for acute exposure and between 450 REMS and 750 REMS for fractionated exposure. Damage to an eye begins at the time of the exposure, and continues to occur for several weeks thereafter, due to the generation of free radical toxins in the eye tissue. Secondary to X-ray induced cataracts, concurrent or subsequent exposure to Ultra-Violet (UV) light will cause photochemical cataracts, while reducing the cataractogenic dose for all types of radiation. Therefore, the danger is increased whenever more than one type of harmful radiation exposure to the eye exists with cumulative effects. Also, shorter wavelength infrared radiation will promote cataract formation. Such an infrared cataract has been termed a glass blower's cataract.

At risk are dental patients undergoing various procedures (including C.T. scan, fluoroscopic, tomographic, cephalometric, panagraphic, full mouth series, bite wing, and occlusal X-ray procedures, and UV radiation induced curing processes), medical patients (as with C.T. scan, fluoroscopic, tomographic, and like techniques), and the dental and medical practioners performing radiation related procedures. Additional at risk individuals include airline pilots, astronauts, people living at higher elevations, nuclear accident or conflict victims, and those persons found in environments where radiation is prevalent.

Various protective eye wear devices exist, but not for reducing all types of cataractogenic radiation, while providing for interdiciplinary use. In each case, only one form of harmful radiation is stopped, allowing the other forms to damage the eye. Combination Gamma, UV, X-radiation, and near blue light protective goggles are desperately needed. The subject invention structure provides the combined protection while incorporating additional desirable elements. More particularly, this device relates to sterilizable goggles having a novel composition and construction comprising a frameless, circularly curved leaded polymer, Gamma, UV, near blue light, and X-ray opaque, yet visible light transmissive lens having an outer perimeter edge associated with a leaded vinyl radiation opaque boot, adjustable and interchangable ear pieces, and a detachable variably sized nose rest.

2. Description of the Background Art

Given sufficient exposure, most radiation is capable of inducing damage to sensitive eye tissue. However, it is documented that the most dangerous range of radiation (in terms of generating tumors, cataracts, and general retinal injury) is near blue visible light and wavelengths less than 525 nm, such as UV-A (320-400 nm), UV-B (280-320 nm), and UV-C (180-280 nm) in the case of photochemical cataract (see, The New England Journal of Medicine, H. R. Taylor, et al., 319(22), pp. 1429-1433 (1988) and Documenta Ophthalmologica, S. Zigman, 55, pp. 375-391 (1983)), and Gamma and X-ray (see, Pathology of the Eye, D. vonDomarus, et al., pp. 227-234, Springer-Verlag, New York (1986), Oral Surgery, S. Antoku, et al., 41(2), pp. 251-260 (1976), Radiation Physics, J. T. Littleton, et al., 129, pp. 795-798 (1978), and Ophthalmology, L. T. Chylack, Jr., 91(6), pp. 596-601 (1984)). Additionally, the foregoing articles establish a cause and effect relationship between radiation exposure and eye damage (tumor, cataract, and retinal injury), while providing data of actual measured dose exposure to eye tissue in REMS (biological equivalent of radiation absorbed dose: ionizing energy transfer of 100 ergs per gram of eye tissue) resulting from irradiation procedures and environmental exposure.

Until now, the problem of combined and cumulative effect multi-type radiation exposure of the eye has not been solved. Traditionally, protective eye devices for preventing UV and X-radiation damage are either totally opaque to visible light, such as a shield of lead foil, or transmissive to visible light and selectively restrictive to either UV or X-radiation. Additionally, most of the prior art devices are not suited for interdiciplinary use because they are cumbersome and heavy, thereby inhibiting easy movement of the wearer, while failing to protect from all angles of exposure.

In general, medical and dental patients fear what they can not see. Some of the prior devices overlooked the desirability and necessity of having a patient observe a procedure so that they may be aware of and respond to spatial commands of head positioning. Due to undesirable angles and construction features, many of the prior art designs that relied on complete visible light, UV and X-ray blockage are not adaptable to visible light transmissive versions. In addition, the problem of lens fogging with condensation occurs with prior art goggles that provide peripheral exposure protection. Further, the prior art goggles do not shield the eyes from all types of cataractogenic radiation.

Disclosed in U.S. Pat. No. 4,024,405 is an X-ray eye shield for protecting eye tissue during dental radiography. The lens cups are constructed of lead encased plastic. These lens cups fit snugly over the patient's eye sockets, therefore, all visible, UV, and X-ray radiation is blocked and the free circulation of condensation preventing air is stopped and fogging occurs.

U.S. Pat. No. 4,635,625 relates a surgical eye mask for laser treatment fabricated from highly reflective metal, preferably aluminum, foil and having eye pads of cotton gauze for maintaining eye moisture. Adhesive means are provided to seal the mask against the patient's face during laser irradiation. Given the radiolucent qualities of aluminum foil, X-radiation is not adequately blocked and all vision is completely blocked.

A hand-held light filter is presented in U.S. Pat. No. 4,640,685. This shield must be held by a dental assistant in front of a patient's mouth during UV irradiation procedures involved in curing dental resins in the patient's mouth. From particular angles, incident scatter UV light may be reflected by the shield back into the patient's eyes with harmful effects. In addition, harmful radiation of less than 400 nm or greater than 525 nm (near blue light) is free to pass through the specific material disclosed in '685.

Depicted in U.S. Pat. No. 4,701,129 is a visible light transmissive face shield device for protecting a dentist's face from debris, bacteria, and the like, including UV radiation from resin curing procedures. Large shoulder supports hold the device in place during use and restrict movement.

U.S. Pat. No. 4,758,079 discloses an eye shield that resembles a pair of ordinary sunglasses. However, the lenses in the device are coated with reflecting and absorbing materials that completely block only direct UV and visible light transmission, while allowing harmful peripheral scatter rays to reach the eye. Additionally, the lens material does not effectively block X-radiation.

Offered for sale in Catalog G-5 from Nuclear Associates (A Division of Victoreen, Inc., 100 Voice Road, Carle Place, NY, 11514–1593) are two types of visible and UV light transmissive, but X-ray opaque glasses. On page 34 is offered, for medical personnel, prescription and nonprescription Radiglasses TM which resemble normal eyeglasses with side shields of the same X-ray opaque heavy leaded glass as used in the front viewing lenses. Close examination reveals that complete peripheral ray protection from many angles is not provided. Additionally, the X-ray opaque frame interferes with the images of important anatomical landmarks necessary for diagnosis in medicine and dentistry. A set of protective lens cups for a patient are offered alternatively on page 48. These lens cups fit tightly over the contours of the orbits of the eye to block peripheral radiation, thereby preventing the exchange of moist air to produce fogging.

SUMMARY OF THE INVENTION

An object of the present invention is to produce safety goggles that effectively reduce, by over 90%, eye exposure to all known types of cataractogenic radiation (near blue light, UV-A, UV-B, UV-C, Gamma, and X-radiation) from all angles of incidence found in the wearer's surrounding environment, while providing unimpaired forward and peripheral vision.

An additional object of the present invention is to create safety goggles that conform to all facial curvatures of a wearer, from children to adults, while providing a peripheral seal.

Another object of the present invention is to make safety goggles that are sterilizable to prevent possible contamination to multiple user patients from organisms that cause A.I.D.S., hepatitis, and other communicable diseases.

Yet another object of the present invention is to fabricate safety goggles that are inexpensive to produce, since the component parts are very inexpensive and no drilling or screws are required for assembly, thereby facilitating widespread adoption and interdiciplinary use.

Yet a further object of the subject invention is to manufacture goggles that have multipurpose applications in dentistry as; UV light curing, X-ray shielding, and general safety goggles, thereby eliminating the need for three different types of glasses in clinical practice.

Yet still another object of the subject invention is assemble goggles with a surrounding UV, Gamma, and X-ray impervious boot that provides ventilation to prevent fogging, yet adapts automatically to a wearer's facial contours to form a peripheral shield.

Yet still a further object of the subject invention is to make protective goggles that have both a radiolucent polymer frame and a lens positioned to avoid blocking critical anatomical landmarks used for graphic calculations in orthodontic and cephalometric X-ray procedures.

Yet still an additional object of the subject invention is to make protective goggles that will encourage an interdiciplinary use to shield astronauts and high altitude pilots from solar flares and storm radiation, and also to provide all purpose goggles for the general public to shield the wearer's eyes from high intensity solar radiation at high elevations.

Disclosed is a pair of protective safety goggles for effectively shielding a user's eye tissue from cataractogenic radiation, comprising a sterilizable, generally flattened and essentially UV, Gamma, and X-ray radiopaque leaded polymer lens having a generally oblong lens-on profile with an elongated outer perimeter border with upper and lower long edges and two opposing short side edges. The frameless lens is formed to curve in the arc, or a circle coextensive with said long edges, over the surface of the user's face to substantially cover both eyes of the user from both frontal and profile views. A sterilizable radiolucent polymer nose rest is reversibly attached in a receiving notch in the lower long edge of the lens midway between the opposing side edges of the lens. Two sterilizable, partially removable, and adjustable radiolucent polymer ear pieces are associated with the lens. Specifically, one of the ear pieces is attached to each of the opposing short side edges of the lens. Additionally, an UV, Gamma, and X-ray radiopaque boot is fastened to the upper and lower long edges of the lens. This boot comprises a plurality of flattened elongated strips of flexible leaded polymer with each of the strips having first and second opposing long margins and opposing short margins, with a tab projecting from at least one short margin of each strip. The first long margin of a strip is secured to the upper long edge and the first long margin of at least two other of the strips is secured to the lower long edge of the outer perimeter border of the lens with all of the strips extending from the outer perimeter lens border to proximate the user's face at the second long margin of each of the strips producing an enclosure. To aid in fastening the strips, the tabs are secured in receiving slots in each hinge piece. The enclosure spans between the opposing short side edges of the lens along the upper and lower long edges having an air vent proximate each of the short side edges, near the area where the tabs are secured. These air vents provide an essentially water condensation free environment within the goggle enclosure.

Other objects, advantages, and novel features of the present invention will become apparent from the detailed description that follows, when considered in conjunction with the associated drawings.

BRIEF DESCRIPTION OF THE DRAWINGS

FIG. 7 is a cross sectional view of a nose piece mounted in a lens of the subject invention.

FIG. 8 is a view of the hinge region of an ear piece of the subject invention.

DESCRIPTION OF THE PREFERRED EMBODIMENT

Figure 1:
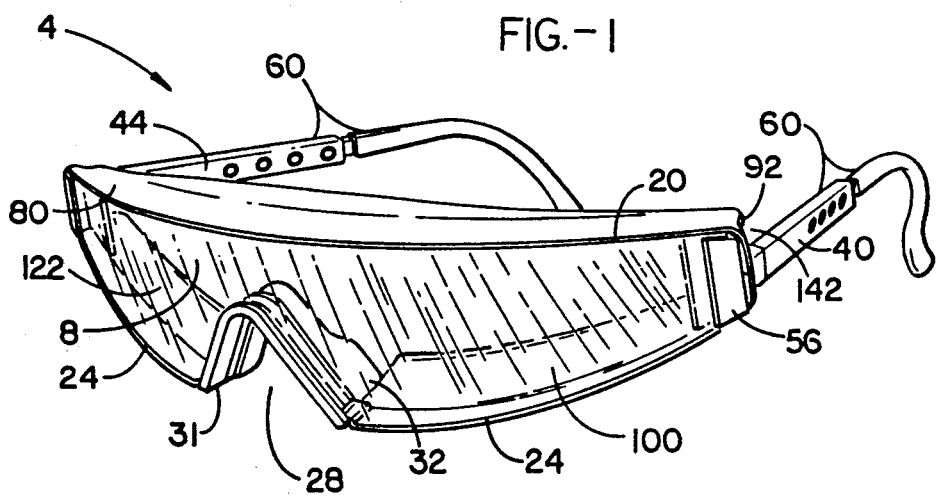
FIG. 1 is a perspective illustration of the subject invention having a surrounding protective boot.
Figure 2:
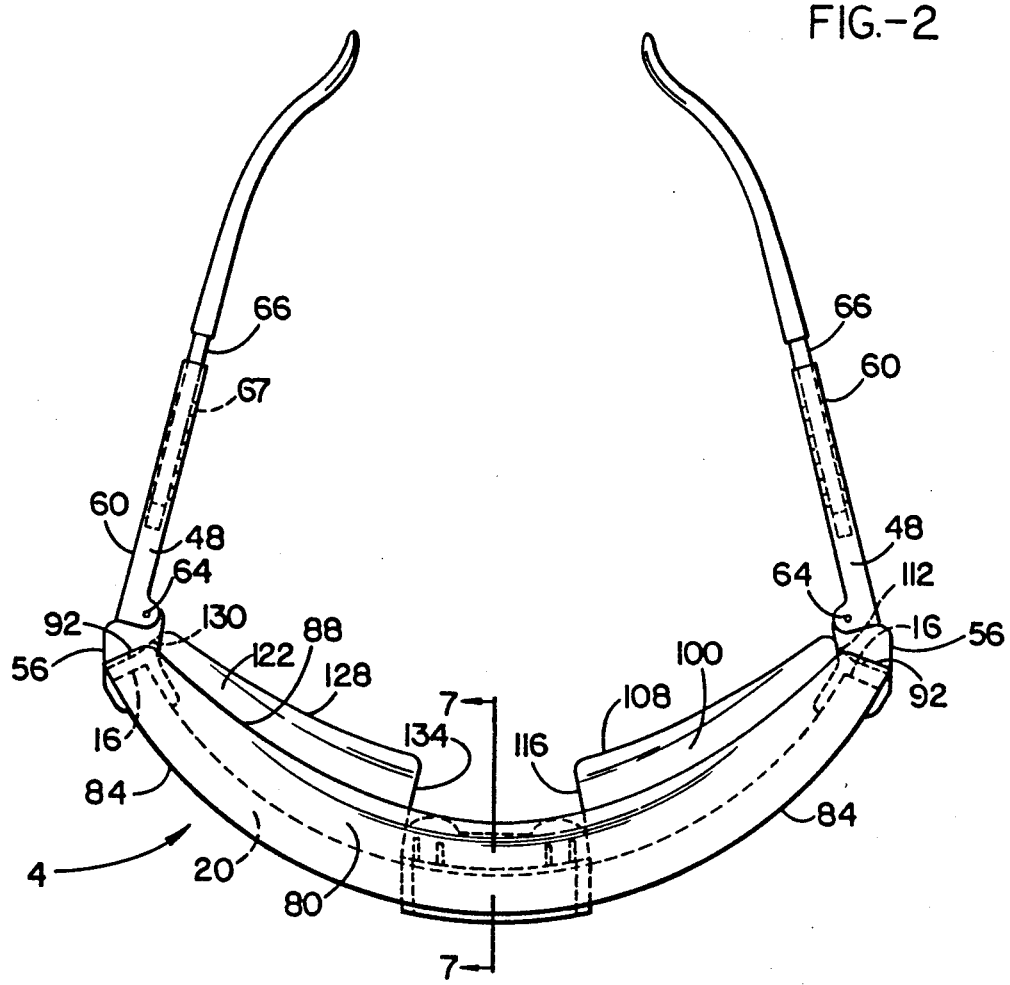
FIG. 2 is a top view of the subject invention.
Figure 3:
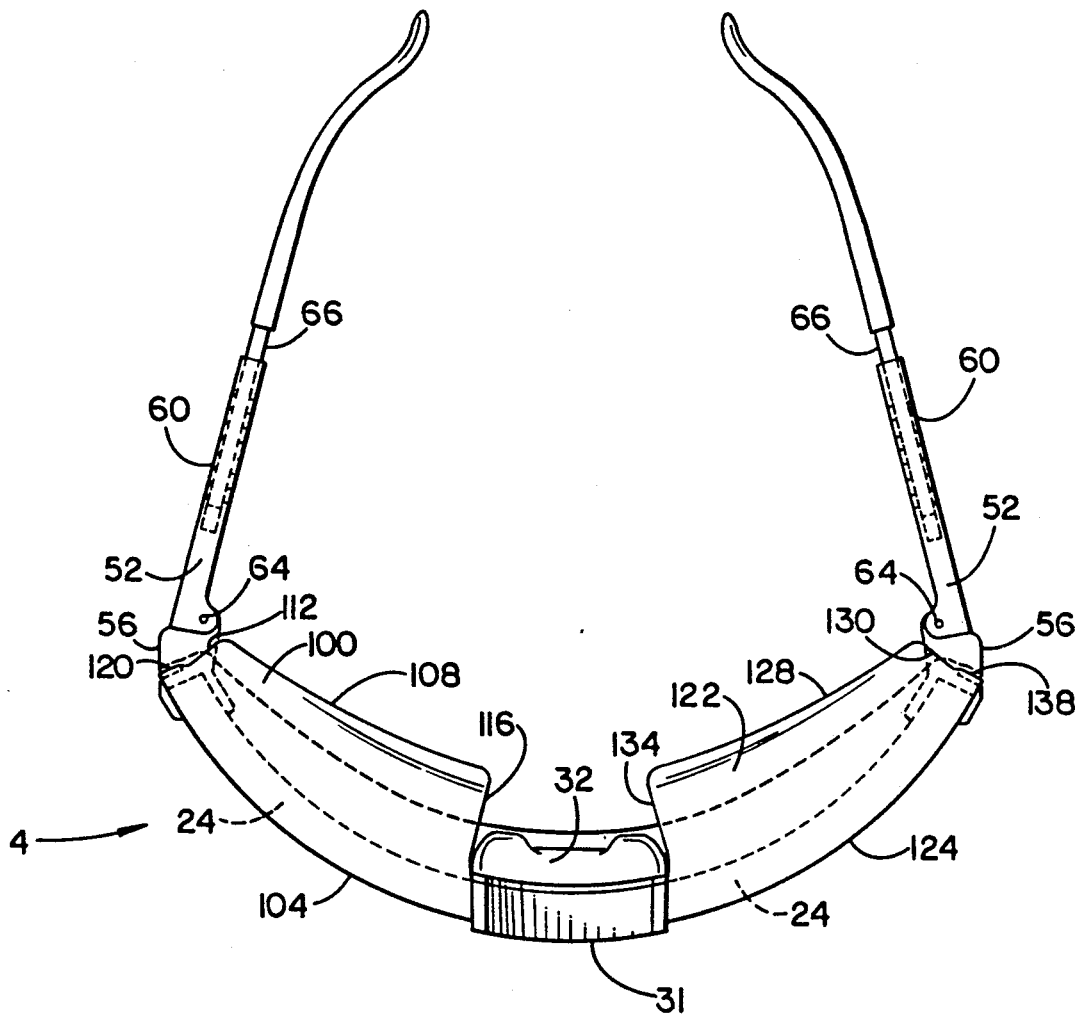
FIG. 3 is a bottom view of the subject invention.

Referring now to FIGS. 1–8, there is shown a preferred embodiment of protective safety goggles 4 of the subject invention. This device is for blocking harmful radiation with a lens 8 having sufficient filtering properties to effectively limit the amount of UV, Gamma, and X-ray radiation that passes through the lens 8 to contact the eye tissue of a wearer. The subject device is intended for utilization by a user or wearer in all environments where UV, Gamma, and X-ray radiation exposure may be encountered and is intended to shield a wearer's eye tissue from such dangerous radiation. Since one use for the subject device is eye protection from UV and X-ray radiation for various patients undergoing dental or medical procedures and any one of these patients might be infected with a communicable disease (such as hepatitis, aids, and like afflictions), the lens 8, all other components, and attachment means of the subject invention are fabricated from materials that resist standard chemical and heat sterilization procedures.

The subject invention, as illustrated in particular in FIGS. 1–6, comprises a lens 8 that is capable of blocking essentially all UV, Gamma, and X-ray radiation that might strike the goggles during an intended use. Blocking essentially all UV radiation is defined for purposes of this device as between about 70% and about 100% of the encountered UV radiation being stopped from passing the goggles 4. For effectively blocking X-rays, the defined level for this device is between about 90% and about 100% elimination of encountered X-rays from striking a user's eye tissue. Gamma rays are effectively blocked by eliminating greater than about 70% of the rays.

The structure of the lens 8 comprises elongated form of generally uniform thickness usually from about 1 mm to about 9 mm, more preferably from about 2 mm to about 8 mm, and preferably about 7 mm. The thickness is dependent upon the ability of the lens 8 to filter harmful UV, Gamma, and X-ray radiation. The lens may be constructed from any suitable material (e.g., glass or polymers that are doped with sufficient quantities UV blockers and lead or similar elements to decrease the transmission of X-rays and Gamma rays) that transmits visible light, but is essentially radiopaque to UV, Gamma, and X-rays. Suitable lens 8 materials comprise between about 20% and about 40% lead by weight. A preferred material for the construction of the lens 8 is an acrylic polymer that contains 30% lead by weight. Although any suitably doped (with X-ray and Gamma ray shielding substances and optionally, known UV blocking agents) plastic polymer would be within the contemplation of this disclosure, a specific example is a 30% lead by weight acrylic copolymer known as CLEAR-Pb ® from Nuclear Associates (Nuclear Associates is a division of Victoreen, Inc., 100 Voice Road, Carle Place, N.Y. 11514–1593) which provides a lead thickness equivalence of about 0.3 mm lead. It is well known that plastic polymers are effective blockers of UV radiation. For example, a 7 mm thickness of the CLEAR-Pb ®, treated with UV blocking agent, effectively filters greater than 70% of UV radiation. The lens may be formed by standard techniques such as casting, thermo-molding, or injection molding.

Surrounding the outer extent of the lens 8 is an elongated outer perimeter border. The lens 8 has two opposing essentially parallel short edges 16 and opposing outwardly or convexly curved upper 20 and lower 24 long edges. The upper 20 and lower 24 long edges appear to bulge away from the lens 8. The lens 8 is formed so that it curves in a smooth arc, coextensive with the long edges 20 and 24, over the surface of a user's face. This curved lens 8 substantially covers both eyes of the user. Since an individual wearer's face does not drastically change in curvature from childhood to adulthood (only enlarges in size, not curvature), one pair of goggles may be used for both children and adults.

In the lower long edge 24, midway between the short side edges 16 is a nose rest receiving notch 26. As seen in particular in FIGS. 1, 4, 6, and 7, mounted within the nose rest receiving notch 26 is a nose rest. To prevent the nose rest from interfering with X-ray pictures, the nose rest is constructed from radiolucent materials such as structurally acceptable polymers and natural and synthetic rubbers. The nose rest comprises a body 31 (preferably constructed of a plastic material) and at least a portion that is a detachable member 32 (preferably constructed of a rubber substance) for easy removal (see, FIG. 7). Because individual wearers of the goggles 4 will have variably sized noses, the detachable member 32 comes in different thicknesses and proportions to accommodate all nose sizes and shapes. The detachable member 32 is secured to body 31 of the nose rest by means that are easily employed, such as grooves, slots, snaps, Velcro ® mating strip, and equivalent devices, and preferably by pins 34 projecting from the body 31 of the nose rest that fit within receiving holes 35 in the detachable member 32. Further, the ability to easily remove the nose rest detachable member 32 allows for ready sterilization (one of the subject invention pieces most likely to carry a contagious agent, the other pieces being the ear pieces described below) by standard techniques without sterilizing the entire pair of goggles 4.

To attach the nose rest within the nose rest receiving notch 28 a radiolucent means is utilized. As with the nose rest itself, the attachment means must be essentially transparent to X-ray radiation. Depending upon the exact medical or dental usage, anatomical reference points are possibly blocked if a radiopaque nose rest or attachment means are employed. Essentially transparent to X-ray radiation is defined for this device to be greater than about 70% transmissive of X-rays. This attachment means is preferably acrylic glue (Super-Glue ®) or equivalent material, but it is well within the realm of this disclosure to employ alternative similar means such as heat, screws, rivets, and the like or to form the nose body 31 as an extension of the lens 8.

Depicted in FIG. 7 is an additional lens coating 37 that may be optionally applied to the surfaces of the lens 8. Primarily, this lens coating 37 is to filter UV and near blue visible radiation (525 nm to UV) from passing through the lens 8. Even though plastic polymer lenses filter UV radiation, additional protection in the range of about 70% to 100% UV blockage is achieved by applying an appropriate standard blocker as a lens coating. Also, it is known that near blue radiation can cause eye damage. A typical lens coating that essentially blocks near blue visible radiation is TLS blue-blocking tint (available from North American Coating Laboratories of California, Inc., 695 S. Raymond Ave., Pasadena, Calif. 91105). Such a near blue coating is applied by standard techniques such as immersion of the lens 8 into a heated (208° F.) bath of TLS for two minutes. Further, infrared blocking tints are commonly available that prevent the passage of radiation in the range of 700 nm to 800 nm and would be applied by standard techniques.

Attached to each lens short side edge 16 is an ear piece. The attachment is by radiolucent means that is similar to or equivalent with the attachment means used to secure the nose rest body 31. As above with the nose rest, depending upon the exact medical or dental usage, anatomical reference points are possibly blocked if radiopaque ear pieces and attachment means are employed. Preferably, the radiolucent attachment means is acrylic glue (Super-Glue ®) or its equivalent, that securely fastens the ear pieces while allowing at least 70% of X-ray radiation to pass. Preferably, the ear pieces are fabricated from radiolucent plastic polymer, but similar materials are contemplated to be within this disclosure.

Each ear piece has a front surface 40, a back surface 44, an upper edge 48, a lower edge 52, a first end region 56, and a second end region 60. At the terminal portion of the first end region 56 closest the lens 8 is where the attachment to the lens short side edge 16 occurs (see, FIG. 8). At the opposite terminal portion of the first end region 56 is one half of a hinge 64 for allowing a user to bend the ear piece. Preferably, the hinge is radiolucent and is either an additional piece added to the ear piece or is formed as a continual element of the polymer ear piece material. At one terminal portion of the second end region 60 is the other half of the hinge 64. Standard hinge technology is employed to couple the two halves of a hinge into a pivotable form. At the opposing terminal portion of the ear piece second end region 60 is a typical area having a form adapted for fitting over or behind a user's ear to secure the goggles 4 in place.

Additionally, the ear pieces are adjustable (not only the terminal portion of the second end region 60, that fits over the user's ear). Each ear piece is able to be lengthened or shortened and secured about a telescoping connection 66, having male and female components, located between the hinge 64 and the terminal portion of the second end region 60. Ear piece length adjustability is achieved by a pressure fit of the telescoping connection 66, wherein, preferably, a plurality of knob-hole interlocking means 67 are positioned along the telescoping connection 66, however, other equivalent means for producing ear piece adjustability are considered to be within the realm of this disclosure. At least one knob on the male component of the connection 66 fits into a hole on the female component of the telescoping connection 66. To fit children or adults, the ear pieces may be extended to an appropriate length and secured by the knob-hole interlocking means 67. (also, a suitable detachable nose rest member 32 would be selected). Since the curvature of a wearer's face stays essentially constant during growth, the extension of the ear pieces can accommodate an adult over a child. Further, the telescoping connection 66 may be separated and at least part of the second end region 60 (from the male component of the connection 66 to the terminal user ear fitting area) removed from the remainder of the goggles 4 for easy immersion cold sterilization.

Within each first end region 56 is an ear piece tab receiving slot 72. This tab receiving slot 72 is formed through the front surface 40 of an ear piece and into the ear piece proximate the first end region 56. The slot 72 extend from the upper ear piece edge 48 to the lower ear piece edge 52. The purpose of a tab receiving slot 72 is to receive a tab that projects from an element of a radiopaque boot to aid in securing the boot to the lens 8.

The preferred embodiment of the subject device includes a radiopaque boot that produces an enclosure that extends from the lens 8 to proximate a user's face, and may touch the skin of the face. Since harmful radiation can enter an individual's eyes from other than essentially straight on, a radiopaque boot or skirt is attached to the upper 20 and lower 24 long edges of the lens 8. Visible light need not pass through this boot.

The boot comprises a plurality of flattened elongated strips of flexible leaded polymer. The boot is preferably fabricated from lead-vinyl or equivalent materials. Lead-vinyl is commonly available in various thicknesses and for suitable flexibility characteristics a thickness of about 1/32 inch is preferred. Such a thickness, 1/32 inch, is equivalent to about 0.25 mm of lead. This thickness, 1/32 inch, or generally in the range of about 1/64 inch to about 1/16 inch, effectively blocks X-ray and Gamma radiation and all UV radiation.

Although the preferred embodiment of the subject invention boot comprises three elongated strips, other combinations of strips are contemplated to be within this disclosure. Specifically, the boot comprises a first strip 80 having first 84 and second 88 opposing long side margins. Further, the first strip 80 has two opposing short side margins 92. The short side margins 92 may have essentially straight parallel, divergent, or convergent borders or may be of irregular contour. Each short side margin of the first strip 80, regardless of its general border shape, has a tab 96 that projects away from the short margin 92. The first strip tab 96 is disposed toward the first long side margin 84.

Creating the upper portion of the boot is the first strip 80. The first long side margin 84 is secured to the top surface of upper long edge 20 of the lens 8 by appropriate fastening means such as glue (specifically acrylic glue like Super-Glue ®), heat, screws, rivets, or similar agents. The tabs 96 at each end of the first strip 80 and a limited portion of the first strip 80 protrude past each lens short side edge 16 to permit the tabs 96 to be inserted into and secured within the ear piece receiving slots 72. As above, the tabs 96 are preferably secured by gluing. The distance between the first strip first long side margin 84 and the second long side margin is selected to approximate the distance between the lens 8 and the face of a wearer and is usually between about 1 cm and about 4 cm and more usually about 2 cm to about 3 cm.

Two radiopaque strips produce the lower portion of the boot. A flattened and elongated second strip 100 is comprised of opposing second strip first 104 and second 108 long side margins 104 and opposing second strip first 112 and second 116 short side margins. The second strip first short side margin 112 has a second strip tab 120 projecting away from the first short side margin 112. The second strip first long side margin 104 is secured (secured by means described above for the first strip 80) to the lens lower long edge 24 and oriented to have the tab 120, and a limited amount of the second strip 100, protruding past a lens short side edge 16. This tab 120 is inserted into and secured within an ear piece tab receiving slot 72. Attached immediately next to the nose rest body 31 or beneath the nose rest body 31 in a recess or indentation in the lens lower long edge 24 is the second strip second short side margin 116. The second strip second long side margin 108 extends to near or touching the user's face.

Additionally, a flattened and elongated third strip 122, comprising opposing third strip first 124 and second 128 long side margins 124 and opposing third strip first 130 and second 134 short side margins. The second 100 and third 122 strips are related to one another by mirror image symmetry and (as with the second strip 100 by analogy) the third strip 122 is secured by the third strip first long side margin 124 to the lens lower long edge 24 (on the opposite side of the nose rest receiving notch). The third strip first short side margin 130 has a third strip tab 138 projecting away from the first short side margin 130. The third strip first long side margin 124 is secured (secured by means described above for the first strip 80) to the lens lower long edge 24 and oriented to have the third strip tab 138, and a limited amount of the third strip 122, protruding past a lens short side edge 16. This tab 138 is inserted into and secured within an ear piece tab receiving slot 72. In mirror image analogy to the second strip 100 above, attached immediately next to the nose rest body 31 or beneath the nose rest body 31 in a recess or indentation in the lens lower long edge 24 is the third strip second short side margin 134. The third strip second long side margin 128 extends to near or touching the user's face.

The distance between the second and third strip first long side margins 104 and 124 and the opposing second long side margins 108 and 128 is selected to span the average distance between the lens 8 and a user's face. This distance is usually from about 1 cm to about 5 cm and more usually between about 2 cm and 4 cm.

Figure 4:
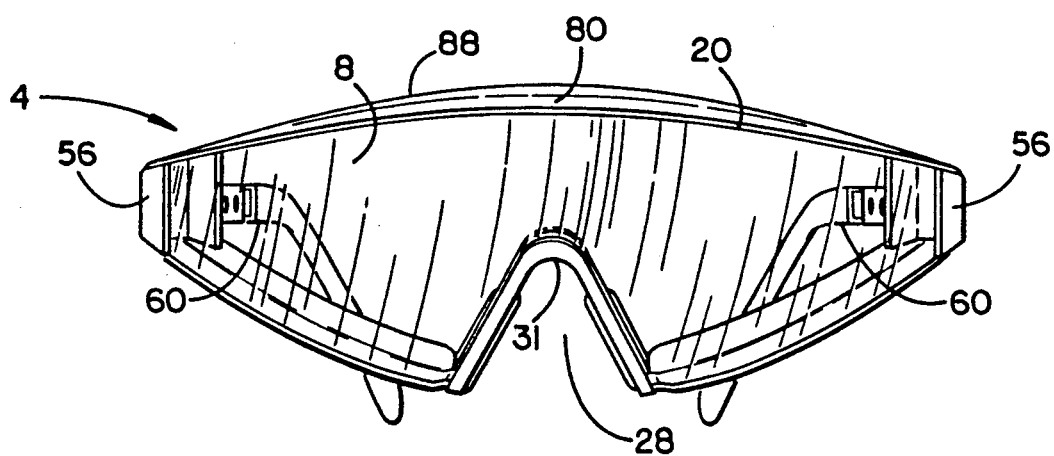
FIG. 4 is a front view of the subject invention.
Figure 5:
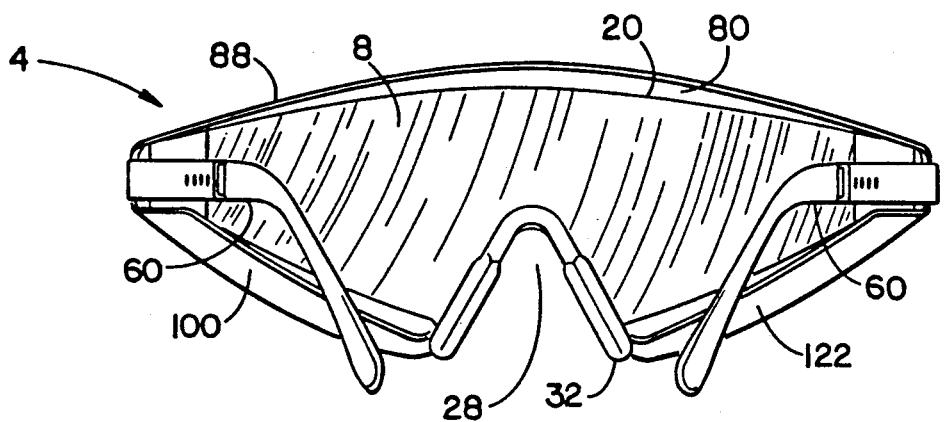
FIG. 5 is a rear view of the subject invention.
Figure 6:
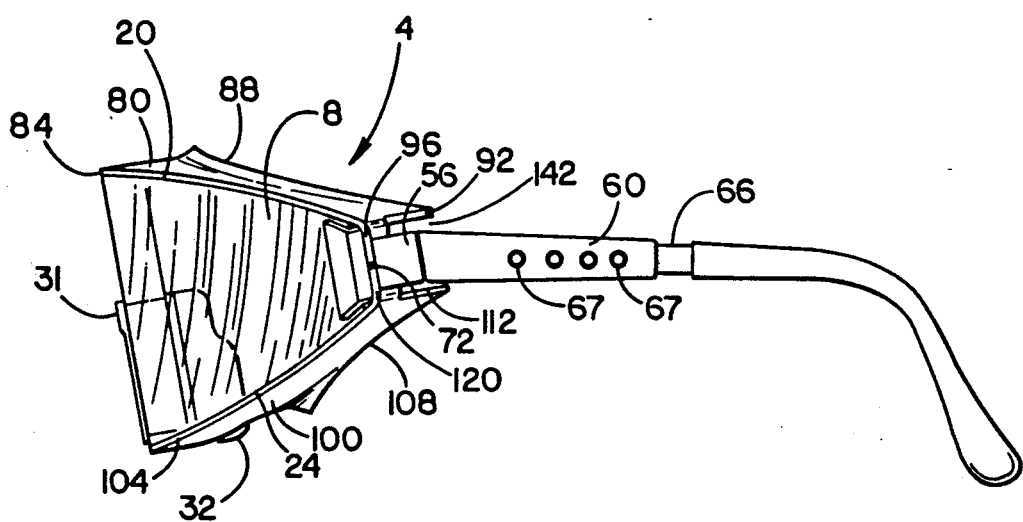
FIG. 6 is a side view of the subject invention.

As seen in particular in FIGS. 1, 4, and 5, an air vent 142 is created proximate each lens short side edge 16 by the three boot strips 80, 100, and 122 that extend from the outer perimeter lens border to proximate the user's face. The enclosure that spans between the lens opposing short side edges 16 along the lens upper 20 and lower 24 long edges provides additional UV, Gamma, and X-ray radiation protection for the user. Additionally, the air vents 142 allow for a ready exchange of air, thereby producing an essentially water condensation free environment for the inside surface of the lens 8.

A typical method of use for the subject device comprises first fitting a user with the above described goggles 4. This process involves selecting the correct detachable nose rest member 32 and adjusting the ear piece adjustment means 66 by extending or contracting the telescoping mechanism. Additionally, each ear piece second end region 60, opposite the half hinge, may need to be bent to fit over a user's ear. Secondly, the goggles are worn where excessive UV, Gamma, or X-ray radiation is encountered. Also, an additional step of sterilization may precede the wearing of the goggles 4.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. Safety goggles for effectively decreasing UV, Gamma, and X-ray radiation exposure to a user's eye tissue, comprising:
   (a) a sterilizable, essentially UV, Gamma, and X-ray radiopaque leaded polymer lens of generally uniform thickness with an elongated outer perimeter border having two opposing essentially parallel short side edges and opposing outwardly curved upper and lower long edges with said lower long edge having a nose rest receiving notch midway between said short side edges, wherein said lens is formed to curve in a smooth arc, coextensive with said long edges, over the surface of said user's face to substantially cover both eyes of said user;
   (b) a sterilizable radiolucent polymer nose rest attached in said receiving notch in said lower long edge of said lens; and
   (c) two sterilizable and adjustable radiolucent polymer ear pieces wherein each of said ear pieces has front and back surfaces, upper and lower edges, and first and second end regions with said first end region having at opposite terminal portions a lens attachment terminal portion and one half of a hinge and said second end region having at opposite terminal portions one half of a hinge that mates with said first end region half hinge to form hinge and an opposing terminal portion having a form adapted for holding over said user's ear whereby each of said ear pieces is attached from said first end region to said opposing short side edge of said lens.

2. Safety goggles according to claim 1, wherein at least a portion of said sterilizable polymer nose rest is a detachable member for easy removal.

3. Safety goggles according to claim 1, wherein said radiolucent polymer ear pieces and nose rest are attached by radiolucent means to said lens.

4. Safety goggles according to claim 1, further comprising a lens coating that essentially blocks near blue visible radiation.

5. Safety goggles according to claim 1, wherein said leaded polymer lens comprises about 20% to 40% lead by weight and approximately 2 mm to 8 mm in thickness.

6. Safety goggles according to claim 1, further comprising:
   (a) a tab receiving slot formed through the front surface and into each of said first end regions and extending from said upper to said lower ear piece edges and
   (b) an UV, Gamma, and X-ray radiopaque boot fastened to said upper and lower long edges of said lens wherein said boot comprises;
   a first flattened elongated strip of flexible leaded polymer having first and second opposing long side margins and opposing short margins having a tab projecting away from each short margin wherein said first long side margin of said first strip is secured to said upper long edge of said lens with said tabs protruding past each of said lens short side edges wherein each of said tabs is inserted into and secured within said ear piece tab receiving slot and
   second and third flattened elongated strips of flexible leaded polymer, said second and third strips being related by mirror image symmetry to each other, with each having first and second opposing long side margins and first and second opposing short side margins with each of said first short side margins having a tab projecting away from said first short side margin wherein said first long side margins of said second and third strips are secured to said lower long edge of said lens with each of said tabs protruding past each of said lens short side edges wherein each of said tabs is inserted into and secured within said ear piece tab receiving slot and said second short side margin attached proximate said lens receiving notch with all three of said strips extending from said outer perimeter lens border to proximate said user's face at said second long margin of each of said strips producing an enclosure that spans between said lens opposing short side edges along said lens upper and lower long edges creating an air vent proximate each of said lens short side edges thereby providing additional UV, Gamma, and X-ray radiation protection for said user in an essentially water condensation free environment.

7. Safety goggles according to claim 6, wherein said flexible leaded polymer comprises lead-vinyl having a thickness equivalent to approximately 0.1 mm to 0.4 mm of lead.

8. Safety goggles for effectively decreasing UV, Gamma, and X-ray radiation exposure to a user's eye tissue, comprising:
  (a) a sterilizable, essentially UV, Gamma, and X-ray radiopaque leaded polymer lens of generally uniform thickness with an elongated outer perimeter border having two opposing essentially parallel short side edges and opposing outwardly curved upper and lower long edges with said lower long edge having a nose rest receiving notch midway between said short side edges, wherein said lens is formed to curve in a smooth arc, coextensive with said long edges, over the surface of said user's face to substantially cover both eyes of said user;
  (b) a sterilizable radiolucent polymer nose rest attached in said receiving notch in said lens lower long edge wherein at least a portion of said nose rest is a detachable member for easy removal;
  (c) two sterilizable and adjustable radiolucent polymer ear pieces wherein each of said ear pieces has front and back surfaces, upper and lower edges, and first and second end regions with said first end region having at opposite terminal portions a lens attachment terminal portion and one half of a hinge and a tab receiving slot formed through said front surface and into said ear piece and extending from said upper to said lower ear piece edges and said second end region having at opposite terminal portions one half of a hinge that mates with said first end region half hinge to form a hinge and an opposing terminal portion having a form adapted for holding over said user's ear and within said second end region a telescoping connection for ear piece length adjustments and separation whereby each of said ear pieces is attached from said first end region to said opposing short side edge of said lens; and
  (d) an UV, Gamma, and X-ray radiopaque boot fastened to said upper and lower long edges of said lens wherein said boot comprises;
  a first flattened elongated strip of flexible leaded polymer having first and second opposing long side margins and opposing short margins having a tab projecting away from each short margin wherein said first long side margin of said first strip is secured to said upper long edge of said lens with said tabs protruding past each of said lens short side edges wherein each of said tabs is inserted into and secured within said ear piece tab receiving slot and second and third flattened elongated strips of flexible leaded polymer, said second and third strips being related by mirror image symmetry to each other, with each having first and second opposing long side margins and first and second opposing short side margins with each of said first short side margins having a tab projecting away from said first short side margin wherein said first long side margins of said second and third strips are secured to said lower long edge of said lens with each of said tabs protruding past each of said lens short side edges wherein each of said tabs is inserted into and secured within said ear piece tab receiving slot and said second short side margin attached proximate said lens receiving notch with all three of said strips extending from said outer perimeter lens border to proximate said user's face at said second long margin of each of said strips producing an enclosure that spans between said lens opposing short side edges along said lens upper and lower long edges creating an air vent proximate each of said lens short side edges thereby providing additional UV, Gamma, and X-ray radiation protection for said user in an essentially water condensation free environment.

9. Safety goggles according to claim 8, further comprising a lens coating that essentially blocks near blue visible radiation.

10. Safety goggles according to claim 8, wherein said leaded polymer lens comprises about 20% to 40% lead by weight and approximately 2 mm to 8 mm in thickness.

11. Safety goggles according to claim 8, wherein said leaded polymer lens comprises about 30% lead by weight and approximately 7 mm in thickness.

12. Safety goggles according to claim 8, wherein said flexible leaded polymer comprises lead-vinyl having a thickness equivalent to approximately 0.1 mm to 0.4 mm of lead.

13. Safety goggles according to claim 8, wherein said flexible leaded polymer comprises lead-vinyl having a thickness equivalent to approximately 0.25 mm of lead.

* * * * *